US00PP20516P2

(12) United States Plant Patent
Utecht

(10) Patent No.: US PP20,516 P2
(45) Date of Patent: Dec. 1, 2009

(54) ***PELARGONIUM* PLANT NAMED 'FISRODEEP'**

(50) Latin Name: *Pelargonium×hortorum*
Varietal Denomination: Fisrodeep

(75) Inventor: Angelika Utecht, Montabaur (DE)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 12/228,729

(22) Filed: Aug. 15, 2008

(51) Int. Cl.
*A01H 5/00* (2006.01)

(52) U.S. Cl. ..... Plt./329

(58) Field of Classification Search ..... Plt./329
See application file for complete search history.

(56) References Cited

OTHER PUBLICATIONS

Upov Plant Variety Database 2009/02. p. 1.*

* cited by examiner

*Primary Examiner*—Annette H Para
(74) *Attorney, Agent, or Firm*—S. Matthew Edwards

(57) ABSTRACT

A new *Pelargonium* plant named 'Fisrodeep,' particularly distinguished by the red-purple flowers with small white eyes, medium sized inflorescences not too high above the foliage, mid season start of flowering, medium green foliage, relatively broad leaves with weak zone, vigorous growth and medium to tall, well-branched, mounding plant habit.

1 Drawing Sheet

Latin name of the genus and species of the plant claimed: *Pelargonium×hortorum.*

Varietal denomination: 'Fisrodeep'.

BACKGROUND OF THE NEW PLANT

The present invention comprises a new zonal Geranium, botanically known as *Pelargonium×hortorum,* and hereinafter referred to by the variety name 'Fisrodeep.'

'Fisrodeep' is a product of a planned breeding program. The new cultivar has deep red-purple flowers with white eyes, medium green foliage with weak zonation, and medium to tall, bushy plant habit.

'Fisrodeep' originated from a hybridization made in the summer 2003 in a controlled breeding program in Hillscheid, Germany. The female parent was the commercial cultivar 'Fistaneon', U.S. Plant Pat. No. 13,188, with red-purple flower color, petals with scarlet bases, dark-green foliage, with weak leaf zone, and moderately vigorous growth.

The male parent of 'Fisrodeep' was an unpatented hybrid seedling identified as 'k97-2235-1' with pink, single-type flowers, and dark green foliage.

'Fisrodeep' was selected as one flowering plant within the progeny of the stated cross in the spring of 2004 in a controlled environment in Galdar, Gran Canaria, Spain.

The first act of asexual reproduction of 'Fisrodeep' was accomplished when vegetative cuttings were taken from the initial selection in the fall of 2004 in a controlled environment in Galdar, Gran Canaria, Spain.

Horticultural examination of plants grown from cuttings of the plant initiated in March of 2005 in Hillscheid, Germany, and continuing thereafter, has demonstrated that the combination of characteristics as herein disclosed for 'Fisrodeep' are firmly fixed and are retained through successive generations of asexual reproduction.

'Fisrodeep' has not been observed under all possible environmental conditions. The phenotype may vary significantly with variations in environment such as temperature, light intensity and day length.

Plant Breeder's Rights for this cultivar was applied for in Canada on Mar. 30, 2007 and in Germany on Feb. 21, 2007. 'Fisrodeep' has not been made publicly available more than one year prior to the filing of this application.

DESCRIPTION OF THE DRAWING

The accompanying photographic drawing shows typical flower and foliage characteristics of 'Fisrodeep' with colors being as true as possible with an illustration of this type. The photographic drawing shows a flowering potted plant of the new variety.

DETAILED BOTANICAL DESCRIPTION

The measurements were taken in Hillscheid/Germany on May 9, 2007 on about 9 week old plants that were growing in a greenhouse. Culture of these plants had started in early March when rooted young plants were planted into 12 cm pots and were grown out, unpinched, at an average day/night temperature of (only) 14° C. until mid of April, and at higher temperature thereafter.

Color Chart used: Royal Horticultural Society Colour Chart (R.H.S.) 2001

BRIEF SUMMARY OF INVENTION

The following observations, measurements, and comparisons describe plants grown indoors and outside in Hillscheid, Germany, and in Chatellerault, France. The following traits have been repeatedly observed and are determined to be basic characteristics of the new variety. The combination of these characteristics distinguishes this *Pelargonium* (common name zonal Geranium) as a new and distinct variety.

1. Red-purple main flower color, upper petals with white 'eyes'
2. Medium sized inflorescences, and large, semi-double flowers
3. Medium green, weakly zoned foliage, and relatively wide leaves
4. Fairly vigorous growth, and medium to tall plant size,
5. Well-branched, mounding habit with the flower heads not very high above the foliage.
6. Mid season spring flowering response
7. Suitable as a bedding plant mainly, or for larger containers

TABLE 1

DIFFERENCES BETWEEN THE NEW VARIETY 'FISRODEEP' AND SIMILAR VARIETIES:

| | 'Fisrodeep' | 'Fisrohot' (U.S. Plant Pat. No. 14,886) Commercial name 'Rocky Mountain Deep Rose' |
|---|---|---|
| Flower color upper petals (RHS) | Between N66B and N74B | N74A-B |
| Leaf zone, distinctness (range from 1 absent to 9 very strong) | Weak (3) | Weak to medium (4) |
| Inflorescences, diameter | 8.9 cm 2007<br>8.9 cm 2008 | 10.0 cm 2007<br>9.2 cm 2008 |
| Foliage canopy, height | 19.2 cm 2007<br>16.0 cm 2008 | 16.4 cm 2007<br>14.5 cm 2008 |
| Number of branches | 7.7 | 4.7 |

| | 'Fisrodeep' | 'Amri Derose Two' (U.S. Plant Pat. No. 15,633) |
|---|---|---|
| Flower color | Mainly between N66B and N74B for upper petals; More pink than N74B for the lower petals | Close, slightly more bluish hue, N74B for upper petals; 72C for lower petals |
| Umbel diameter | 8.9 cm | 10.0 cm |
| Leaf zone, distinctness | Weak | Weak to very weak |
| Leaf shape | Wider, kidney-shape | Somewhat smaller, rounder |

Plant:

*Form, growth and habit.*—Vigorous growth, bushy, well-branched and mounding habit, medium to tall in size.

*Plant height.*—19.2 cm.

*Plant height (inflorescence included).*—Approximately 25 cm.

*Plant width.*—29.5 cm.

*Plant height at the end of the summer (6 months old, on August 28).*—28 cm.

*Plant width at the end of the summer.*—About 30–40 cm in diameter.

Stem:

*Number of branches.*—7.7.

*Color of stem.*—Light green, RHS 143C, no anthocyanin.

*Length of stem.*—Approximately 10–17 cm.

*Diameter.*—0.9–1.8 cm.

*Length of internodes.*—2–3 cm.

*Texture.*—Covered with sparse, short hair.

Foliage:

*Immature, leaf color, upper surface.*—RHS 137D Lower surface: RHS 138A.

*Mature, leaf color, upper surface.*—RHS 137B–137C Lower surface: RHS 138A.

*Length.*—6.8 cm.

*Width.*—11.5 cm.

*Shape.*—Kidney-shape (reniform), with weak lobes, and with wide open base, wavy margins and palmate venation.

*Base shape.*—Cordate.

*Apex shape.*—Rounded.

*Margin.*—Bi-crenate, distinctly wavy.

*Texture.*—Velvety, both surfaces pubescent.

*Color of zone.*—Olive to brown, RHS 147A or 166A.

*Color of veins, upper surface.*—RHS 138D, indistinct.

*Color of veins, lower surface.*—RHS 145A.

*Petiole, color.*—143B to 143 C.

*Petiole, length.*—Approximately 5–6 cm.

*Diameter of petiole.*—3 mm.

*Texture.*—Densely covered with short hair (hirtellous).

Inflorescence:

*Begin of flowering (50% of plants with open flowers).*—On May 4 (8 weeks old).

*Duration of flowering.*—Continuous flowering throughout the Summer.

*Number of inflorescences per plant.*—2 (at the stated time); About 25 in late summer.

*Type and shape of inflorescence.*—Umbel, semi-sphere.

*Number of flowers and buds per inflorescence.*—About 15–20.

*Umbel diameter.*—8.9 cm.

*Umbel depth.*—6–6.5 cm.

*Color of peduncle.*—RHS 143C to 144A.

*Length of peduncle.*—14.8 cm.

*Peduncle diameter.*—3 mm.

*Texture.*—Both glandular hair and soft hair.

*Color of pedicel.*—At base most often green, RHS 144B, main portion reddish-brown, RHS 179A or 181A.

*Length of pedicel.*—2.8 cm.

*Diameter of pedicel.*—1.5 mm.

*Texture.*—Short glandular hair.

Corolla:

*Form.*—Semi-double, weakly cup-shaped, not quite round, but with a gap between upper petals and lower petals.

*Flower diameter.*—5.2 cm.

*Depth of flower.*—1.5–1.7 cm.

*Number of petals.*—5–8.

*Color upper petals, upper surface.*—Intermediate between RHS N66B and N74B, White to pale pink bases, RHS 155D to RHS 69B, size about ⅓ of the petal.

*Color upper petals, lower surface.*—RHS 67B or 71D.

*Length of upper petals.*—2.5–2.6 cm.

*Width of upper petals.*—2.0–2.2 cm.

*Color lower petals, upper surface.*—Slightly more pink than RHS N74B.

*Color lower petals, lower surface.*—RHS 67B.

*Length of lower petals.*—2.5–2.6 cm.

*Width of lower petals.*—1.9–2.0 cm.

*Petal shape.*—Obovate.

*Apex shape.*—Rounded.

*Margin.*—Entire.

*Petal texture.*—Smooth, glabrous.

*Number of petaloids.*—Occasionally 1 or 2, narrower and smaller than petals.

*Color of petaloids.*—N72C upper side, N74C lower side.

Bud (just before opening):
*Color.*—N66B to nearly N74B.
*Length.*—Up to 20 mm.
*Width.*—Up to 1.1 cm.
*Shape.*—Elliptical.

Calyx:
*Number of sepals.*—5.
*Color of sepals.*—Mainly green, RHS 144B; 179A at base.
*Length of sepals.*—1.1–1.2 cm.
*Width of sepals.*—4 mm (largest sepal), 2–3 mm for the other ones.
*Sepal shape.*—Lanceolate.
*Apex shape.*—Acute.
*Margins.*—Entire.
*Texture.*—Both glandular hair and soft long hairs.

Reproductive organs:
*Pistil.*—1.
*Length.*—7 mm.
*Style color.*—RHS 53C.
*Style length.*—3–4 mm.
*Stigma color.*—(Deep) red, RHS 53A.
*Number of stamen.*—7.
*Length of anthers.*—2–3 mm.
*Anther color.*—RHS 47A.
*Length filaments.*—6–8 mm.
*Color of filaments.*—Nearly white, RHS 69D, at base; upper part pink, RHS 68A.
*Pollen amount.*—Moderate (usual amount for the species).
*Color of pollen.*—RHS 25B, yellow orange.
*Fertility/seed set.*—No seed observed.

Disease/pest resistance: Disease resistance or susceptibility other than typical for the species has not been observed on this hybrid

What is claimed is:

1. A new and distinct variety of *Pelargonium* plant named 'Fisrodeep,' substantially as illustrated and described herein.

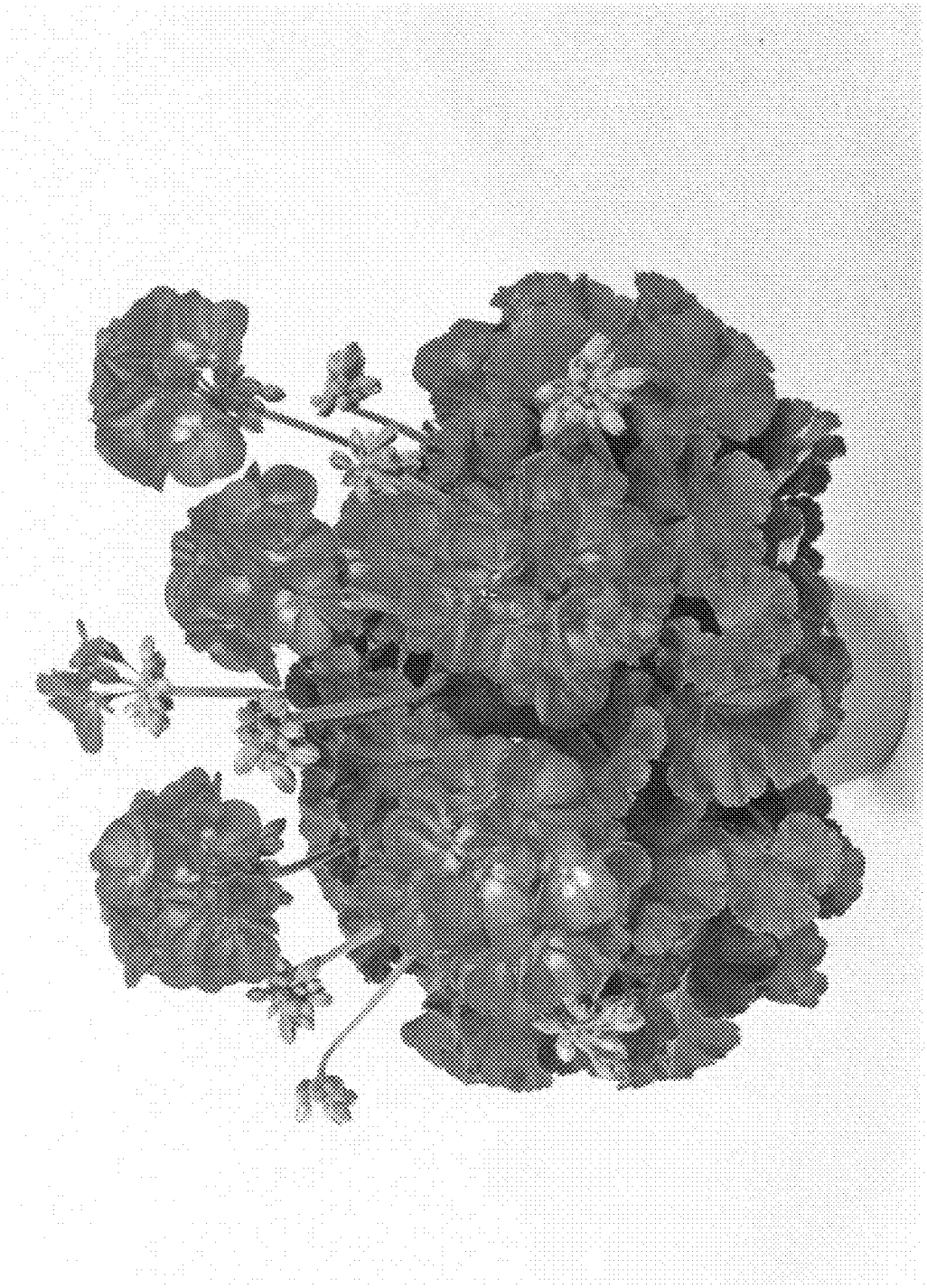

* * * * *